United States Patent
Ott (10) Patent No.: US 7,303,553 B2
(45) Date of Patent: Dec. 4, 2007

(54) DEVICE FOR CONNECTING A CANNULA MADE OF A FLEXIBLE MATERIAL WITH A TUBE

(75) Inventor: Friedrich Ott, Berlin (DE)

(73) Assignee: Berlin Heart GmbH, Berlin (DE)

( * ) Notice: Subject to any disclaimer, the term of this patent is extended or adjusted under 35 U.S.C. 154(b) by 403 days.

(21) Appl. No.: 10/366,827

(22) Filed: Feb. 14, 2003

(65) Prior Publication Data

US 2004/0087986 A1    May 6, 2004

(30) Foreign Application Priority Data

Jun. 24, 2002    (DE) ................................. 102 28 918
Jun. 24, 2002    (DE) ............................ 202 09 987 U (51) Int. Cl.
*A61M 25/16*    (2006.01)
(52) U.S. Cl. ......................................................... 604/533
(58) Field of Classification Search ........ 604/533–539, 604/905, 326, 206
See application file for complete search history.

(56) References Cited

U.S. PATENT DOCUMENTS

| | | | | |
|---|---|---|---|---|
| 2,933,333 A | * | 4/1960 | Bredtschneider et al. ....... | 285/3 |
| 4,022,205 A | * | 5/1977 | Tenczar ........................ | 604/411 |
| 4,161,949 A | * | 7/1979 | Thanawalla .................. | 604/411 |
| 4,969,879 A | * | 11/1990 | Lichte ......................... | 604/533 |
| 5,137,524 A | * | 8/1992 | Lynn et al. ................... | 604/533 |
| 5,181,751 A | * | 1/1993 | Kitamura ...................... | 285/39 |
| 5,318,332 A | * | 6/1994 | Hohmann et al. ............. | 285/24 |
| 5,431,641 A | * | 7/1995 | Grozinger et al. ........... | 604/533 |
| 5,437,650 A | * | 8/1995 | Larkin et al. ................ | 604/536 |
| 5,492,147 A | * | 2/1996 | Challender et al. ..... | 137/614.05 |
| 5,591,137 A | * | 1/1997 | Stevens ....................... | 604/296 |
| 5,599,328 A | * | 2/1997 | Stevens ....................... | 604/533 |
| 5,820,614 A | * | 10/1998 | Erskine et al. .............. | 604/533 |
| 5,868,433 A | * | 2/1999 | Matkovich ..................... | 285/3 |
| 5,957,898 A | * | 9/1999 | Jepson et al. ................ | 604/256 |
| 5,961,497 A | * | 10/1999 | Larkin .......................... | 604/246 |
| 6,394,992 B1 | * | 5/2002 | Sjoholm ...................... | 604/411 |
| 6,440,107 B1 | * | 8/2002 | Trombley et al. ........... | 604/256 |
| 6,641,574 B2 | * | 11/2003 | Badia Segura .............. | 604/533 |
| 6,843,513 B2 | * | 1/2005 | Guala .......................... | 285/332 |

* cited by examiner

*Primary Examiner*—Nicholas Lucchesi
*Assistant Examiner*—Theodore J. Stigell
(74) *Attorney, Agent, or Firm*—Brinks Hofer Gilson & Lione (57) ABSTRACT

A device for connecting or disconnecting cannula to or from a tube. The connection is uncomplicted, quick, safe and provides reproducible conditions in a surgical procedure for connecting to a blood pump that assists the heart or replaces the heart. A nipple (4) is formed on the tube (5) which is inserted into the cannula (7). A rotatable claw ring (1), which is arranged on a cannula end (71) for displacement to a stop (2, 62), can be rotatably joined with a locking ring (3) which is secured to a tube end (51) by axial movement and latching engagement with the locking ring (3). The connection is releasable by rotating the claw ring (1) and pulling the claw ring (1) and the cannula apart in an axial direction.

21 Claims, 11 Drawing Sheets

DEVICE FOR CONNECTING A CANNULA MADE OF A FLEXIBLE MATERIAL WITH A TUBE

BACKGROUND OF THE INVENTION

The invention relates to a device for connecting a cannula (and/or tube) made of a flexible material with a tube.

Devices for connecting cannulae and tubes are known in the art. Frequently, the tubes and/or cannulae are connected with union nuts. A union nut is used in combination with a collet or a hose coupling (butt joint) for connecting tubes and/or cannulae with each other. A radial force is transferred to the cannula when the union is tightened. A union nut enables axial retention and provides a radial seal. This joining technique in particular is currently used for connecting implantable blood pumps which usually require connections between a typically metallic tube and a cannula made of a flexible material.

Such conventional connection between blood pump and cannulae and tube has the following disadvantages:

a thread requires a greater wall thickness. This increases the diameter at the joint and also the weight since more material is required.

the conditions for making the connection are not reproducible and the connections lack stability over a longer time period. A defined tightening torque is possible only within certain limits. Disadvantageously, a torque wrench may have to be used, requiring the surgeon to use an additional tool for implantation and explantation. Since the tightening torque is not specified, the material can be damaged when the connection is tightened excessively (silicone flows under large forces, and woven polyester fabric as well as Dacron® or PTFE can tear). Otherwise, the nut can also be too loose.

in the absence of a rotation interlock, the union nut can become loose due to vibrations. This would inevitably lead to a life-threatening leakage, since the nut can no longer provide the axial retention and the radial seal.

the union nut customarily has a fine thread, resulting in a long threading length. Handling the nut is therefore difficult and time consuming for the surgeon.

union nuts can cause ill-defined and blood-damaging transitions. This can lead to hemolysis and thrombosis.

union nuts are always matched to the specific material of the cannulae (titanium, woven polyester-PTFE, Dacron®, silicone or polyurethane). Other cannula materials require different configurations.

in current systems, the length of the outlet cannula can only be adapted to the anatomy of the patient at the distal end (aorta side). Accordingly, the head of the outlet cannulae can no longer be freely configured. This can result in an undefined and blood-damaging transition, for example, when the outlet cannulae are made of woven polyester cloth. In addition, the outlet cannulae can be kinked, resulting in a reduced blood flow.

It is therefore an object of the invention to provide a device for connecting cannulae made of flexible materials with tubes, which provide uncomplicated, quick, safe and reproducible conditions for connecting and disconnecting the cannula from the tube and vice versa, in particular in connection with a surgical procedure for connecting to a blood pump that assists the heart or replaces the heart.

SUMMARY OF THE INVENTION

The device according to the invention for connecting a cannula made of a flexible material with a tube, wherein a nipple, for example a hose coupling, is inserted into the cannula, is characterized in that a claw ring which is arranged on a cannula end for rotation and displacement to a limit stop, can be joined a locking ring which is secured to a tube end by axial movement and latching on the locking ring. The optionally curved cannula can be arbitrarily rotated about its longitudinal axis relative to the claw ring, so that the location and position of pump and cannula in the body of the patient can be optimally adapted to the anatomical conditions. The seal between the hose coupling and the cannula is generated by radial pressure of the cannula which expands elastically when placed of the hose coupling.

Advantageous embodiments are recited in the dependent claims.

According to an advantageous embodiment of the invention, a tension ring is arranged on the cannula end and fixedly connected with the cannula. The claw ring is arranged on the tension ring for displacement and rotation. The shape and material selected for the tension ring can advantageously support the radial seal by producing additional radial sealing forces.

It is feasible to make the tension ring of an elastic material, e.g. silicone, or of an inflexible material, e.g. metal. In particular, tension rings made of metal can be formed as a slotted sleeve.

According to another embodiment of the invention, the limit stop is formed as a separate collar on the cannula end, so that during latching engagement, the claw ring pushes the end of the collar against the locking ring, thereby providing a tightly sealed connection.

According to another embodiment of the invention, a spacer ring which during the latching operation presses against the collar can be arranged between the collar and the claw ring. The pressure distribution is improved by the spacer ring if the collar is made of a flexible material. The spacer ring can be installed so as to be both displaceable and rotatable, but can also fixedly connected with the claw ring.

According to another embodiment of the invention, a reinforcement element is disposed on the cannula end, wherein the reinforcement element is fixedly connected with the cannula and can be displaced and rotated on the claw ring. Advantageously, the reinforcement element combines the tension ring with the collar.

According to another embodiment of the invention, a groove which receives the spacer ring is provided between the tension ring and the collar. The spacer ring can have different shapes which can be adapted to the specific design requirements. The spacer ring is pressed into the groove by deforming the flexible collar. When the claw ring latches, it presses against the spacer ring which in turn presses against the collar and forms a tight connection with the locking ring. The radial seal is enhanced by the elastically expanded cannula and the tension ring, in this case by the axial seal as a result of the sealing surfaces on the collar.

Alternatively, an axial seal can be provided only at the end face of the collar. The nipple extending into the cannula, which for example implemented as a hose coupling, can then be extremely short or can be eliminated entirely, thereby advantageously reducing the overall length of the heart support system.

According to another advantageous embodiment of the invention, the claw ring includes a base ring with claws having claw holding surfaces being arranged on the base ring via resilient joints. The spacer ring can also be firmly connected with the base ring.

In another advantageous embodiment of the invention, the locking ring includes holding faces which are contacted by the claw holding faces of the claw ring.

According to another embodiment of the invention, the reinforcement element is made of a flexible material, advantageously of the same material used for making the cannula, preferably silicone.

According to another embodiment, the reinforcement element is an integral component of the cannula end, which can be produced, for example, by injection molding, so that the cannula and the reinforcement element are then made of the same material.

According to another embodiment, the locking ring includes sloped faces, which during rotation of the claw ring relative to the locking ring cause the claws to spread apart, so that the claw ring can be pulled off the locking ring, after the claws have disengaged from the sloped faces the locking ring. The connection is thereby unlatched.

According to another embodiment of the invention, the locking ring includes a rotation limit stop which is contacted during rotation of the claw ring relative to the locking ring by a claw that is not spread apart, thus preventing the claw ring from being rotated beyond the unlatching position. A second identical limit stop can be arranged mirror-symmetrically, so that the rotation in the unlatching position is limited independent of the rotation direction of the claw ring.

In another advantageous embodiment of the invention, the cannula includes two or more successively arranged reinforcement elements. This has the advantage that the cannula can be shortened during the implantation process of the pump without having to push an additional reinforcement part onto the cannula end.

The invention has the following advantages:

it is possible to implement a simple, quicker and safe connection of a flexible hollow tube with a metal tube under implantation conditions for a blood pump, wherein this connection can be released by rotating the claw ring and pulling the claw ring off the cannula in an axial direction.

the outside diameter at the connection location between the cannula and the tube increases by only a small amount relative to the outside diameter of the cannula or of the tube, respectively, which reduces the weight.

the connection conditions are reproducible.

the axial retention and the radial and/or axial seal are separate, unlike with connections using a union nut.

the claw ring guarantees axial retention and prevents the connection from separating. The radial and/or axial seal is achieved by optimizing the diameter ratio and/or thickness ratio at the nipple (hose coupling) and at the cannula. As a result, no undefined axial or radial force is applied to the cannula, i.e. the material of the cannula is not adversely affected. Also eliminated is an additional rotation lock, since the claw ring would have to be rotated for releasing the connection, which would require a torque that can spread the claws by sliding of the sloped faces of the locking ring. If necessary, this torque can be supplied by the operator. Accordingly, this represents a self-locking arrangement.

with the snap connection according to the invention, an ideal and gentle transition from the cannula to the tube can be achieved. The connection between the nipple in the form of a hose coupling, which is typically made of titanium, and the cannula have practically zero flow resistance.

the device according to the invention can operate with any known cannula material and does not require substantial design changes no special tool is required for coupling and decoupling the device according to the invention the length of the outlet cannula is adapted at the pump end by cutting off unnecessary reinforcement elements. The claw ring is then again pushed on the cannula and the spacer element is inserted into the groove closest to the cannula end. The outlet end of the cannula can then be designed without restraint.

BRIEF DESCRIPTION OF THE DRAWINGS

The invention will be described in greater detail with reference to an embodiment and the drawings.

It is shown in

FIG. 1a schematically, a axial cross-sectional view of an end of a cannula before joining, FIG. 1b schematically, a axial cross-sectional view of the tube end before joining, FIG. 1c schematically, a axial cross-sectional view of the joint between the cannula end with the tube end according to the invention, FIG. 2 a perspective view of a claw ring, FIG. 3a an axial cross-sectional view of a cannula end with spacer ring, FIG. 3b an axial cross-sectional view of a cannula end with cannula reinforcement without a spacer ring, FIG. 3c an axial cross-sectional view of a spacer ring, FIG. 4a a perspective view of a locking ring as viewed towards the tube end, FIG. 4b a perspective view of a locking ring as viewed towards the cannula end, FIG. 5a an axial cross-sectional view of a claw ring, FIG. 5b an axial cross-sectional view of a locking ring, FIG. 5c an axial cross-sectional view of a claw ring and locking ring in a latched state, FIG. 6a an arrangement of the claws when pushed onto the locking ring (latching position), FIG. 6b an arrangement of the claws on the locking ring after a rotation of the claw ring in an unlatched position, wherein one claw is not spread open and contacts the rotation limit stop, thereby defining the unlatching position, FIG. 7a an arrangement of several cannula reinforcements on a cannula, FIG. 7b an embodiment of a cannula with reinforcement elements connected integrally with the cannula by injection molding, FIG. 8a an illustration of the cannula end with collar and claw ring, FIG. 8b an illustration of the tube end with locking ring, FIG. 8c an illustration of the connection between a cannula end with a tube end with a limit stop at the cannula end, FIG. 9a an illustration of a cannula end with collar and tension ring as well as spacer ring, FIG. 9b an illustration of a tube end with locking ring, FIG. 9c an illustration of the connection between the cannula end and the tube end with collar, tension ring and spacer ring, FIG. 10a an illustration of a cannula end with a narrow collar and claw ring, FIG. 10b an illustration of a tube end with shortened nipple, FIG. 10c a connection arrangement between the cannula end and the tube end with shortened nipples, FIG. 11a schematically, a illustration of a heart assist pump with connection positions according to the invention and outlet elbow, and FIG. 11b a heart assist pump with connection positions and an outlet cannula with several reinforcement elements.

DETAILED DESCRIPTION OF THE PRESENTLY PREFERRED EMBODIMENTS

Figure 1:
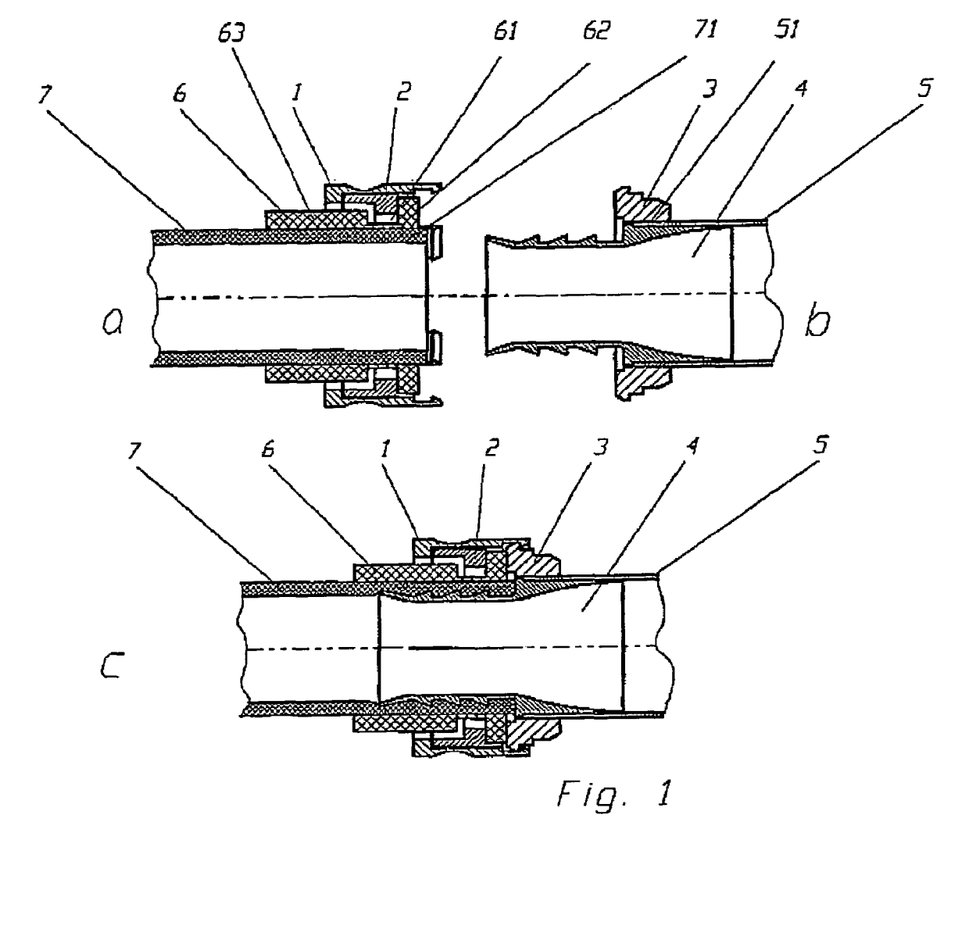

FIGS. 1a, 1b, 1c show an exemplary device according to the invention which provides a connection between a cannula 7 and a tube 5. A nipple, shown here as a hose coupling 4, is inserted in a cannula end 71 (see FIG. 1c). A reinforcement element 6 is disposed on the cannula end 71 and fixedly connected with the cannula end 71. A spacer ring 2 is arranged in a groove 61 of the reinforcement element 6. A claw ring 1 is latched with its claws 11 on the locking ring 3, with the claws 11 of the claw ring 1 being attached to a base ring 15 (see FIG. 2). The claw ring 1 presses hereby on the spacer ring 2 which in turn presses on a collar 62 of the reinforcement element 6, thereby forming a tight connection with an annular end face 36 of the locking ring 3. The seal between the cannula 7 and the hose coupling 4 is formed by an elastic expansion of the cannula end 71, when the cannula end 71 is pushed onto the hose coupling 4. This produces radial sealing forces that press the inner surface of the cannula end 71 onto the hose coupling 4. The radial sealing force is further increased by the tension ring 63 of the reinforcement element 6.

Figure 5:
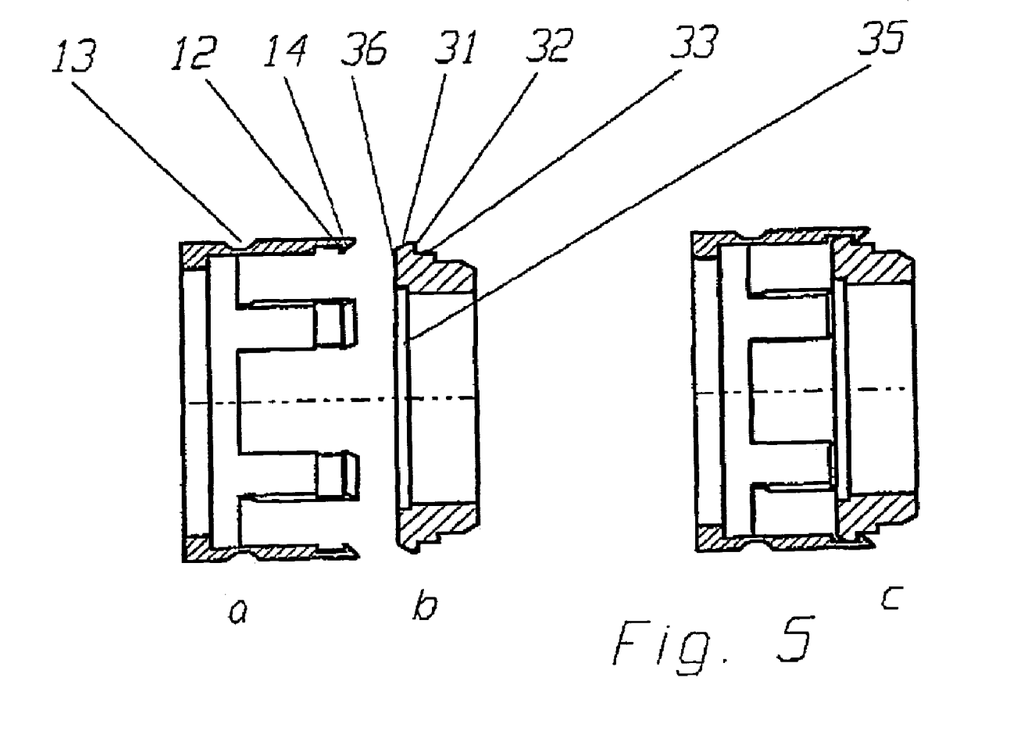
Figure 6:
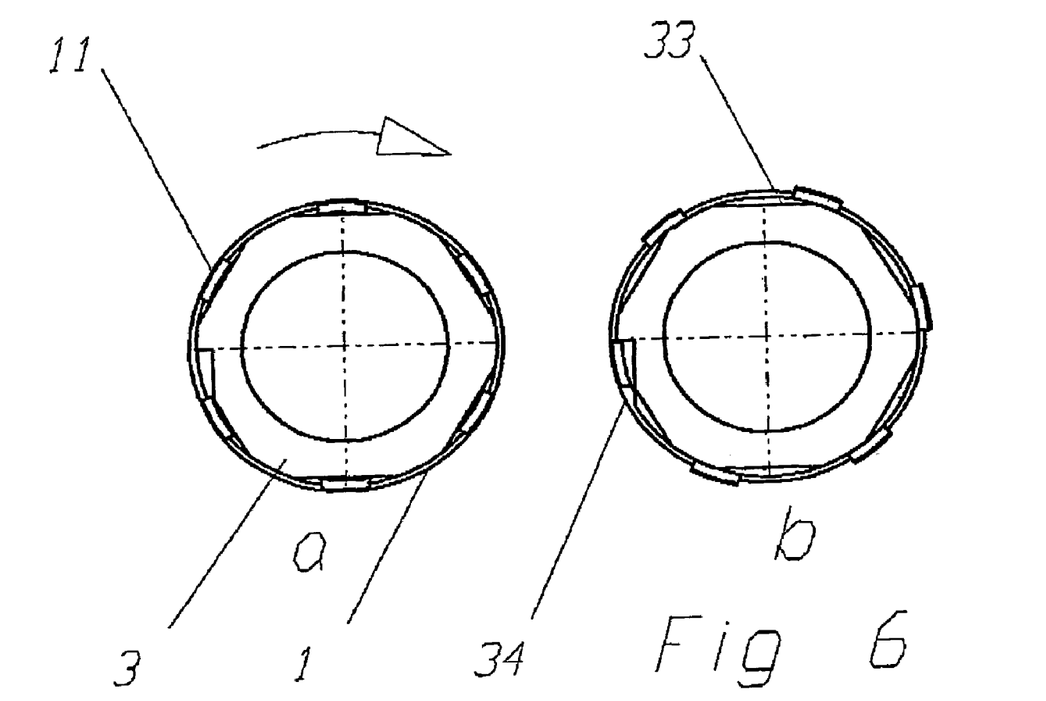

The device according to the invention is essentially a snap connection. The claws 11 disposed on the base ring 15 are pushed over the locking ring 3, where they releasably latch (see FIG. 2, FIG. 5 and FIG. 6).

Figure 7:
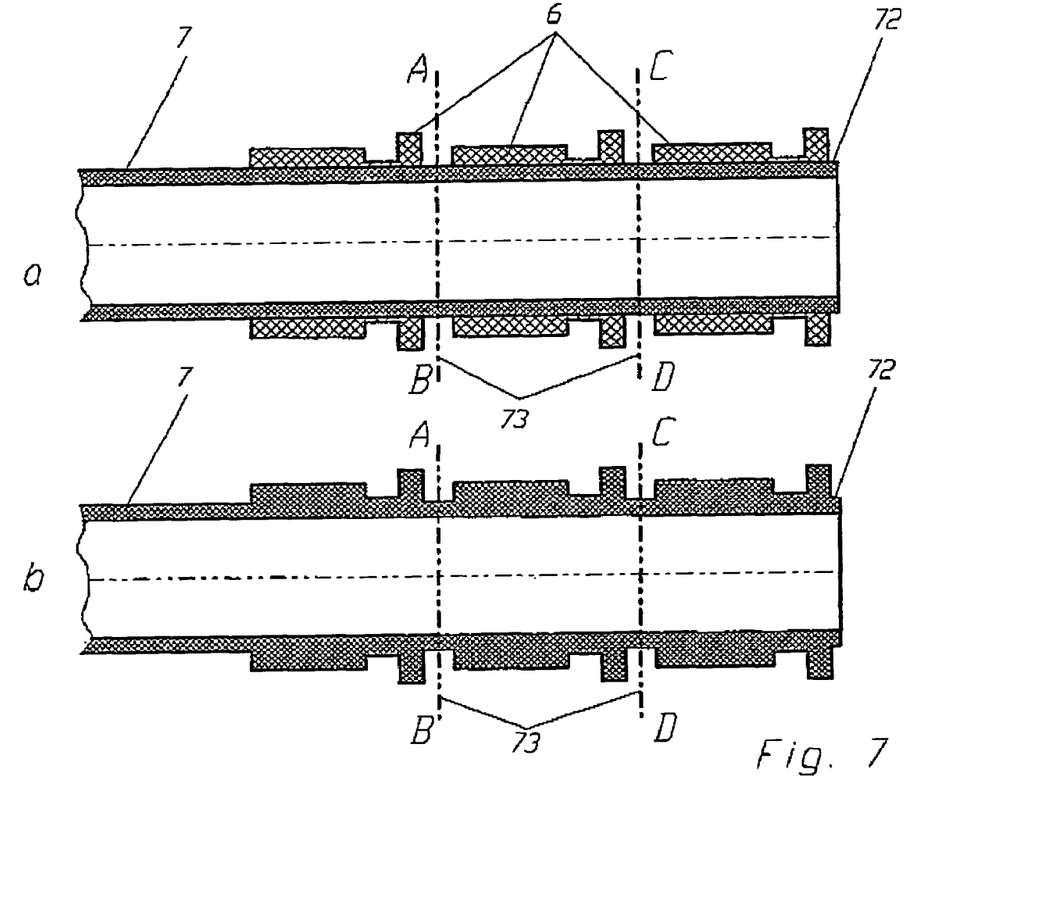

The end face 36 transitions radially outwardly into a sloped face 31 and radially inwardly into a clearance 35, which receives the cannula shoulder 72 disposed before the collar and produced when the cannula is shortened during implantation (FIG. 7). Holding faces 32 and sloped faces 33 are disposed behind the end face 36, with the claws 11 of the claw ring 1 disposed on the cannula snapping into the faces 32 and 33, thereby connecting the cannula 7 with the tube 5. The spacer ring 2 and the claw ring 1 for connecting the cannula 7 can already be premounted on the cannula 7 when the cannula is supplied or can alternatively be mounted on the cannula 7 during surgery. For making the connection, the cannula 7 is pushed onto the hose coupling 4, thereby elastically widening the inside diameter of the cannula 7. The claw ring 1 is rotated until it is positioned relative to the locking ring 3 in the latching position (FIG. 6a), and is then axially displaced towards the locking ring 3. The claws 11 are spread apart when pushed onto the sloped faces 31 of the locking ring and latch with claws support surfaces 12 on the locking ring holding surfaces 32 (FIGS. 5a, 5b, 5c).

Figure 2:
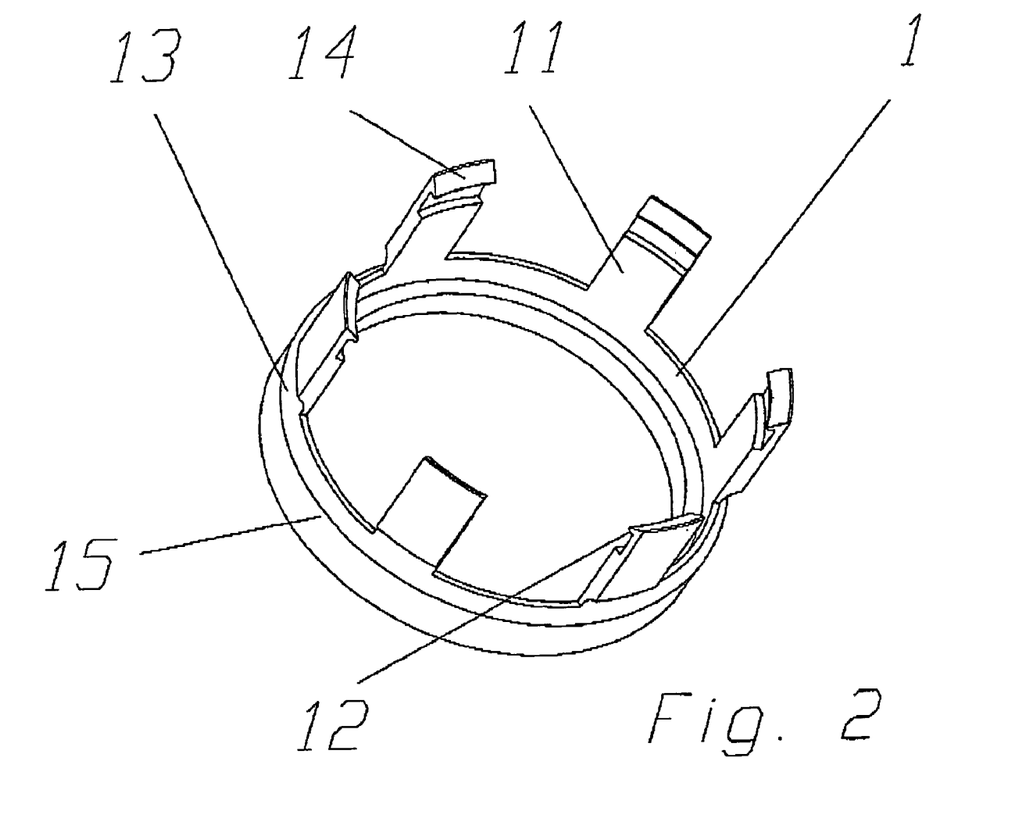

In a perspective illustration of the claw ring 1 according to FIG. 2, six claws 11 are arranged on a base ring 15. The claw holding surface 12 and a sloped claw surface 14 are disposed on the ends of the claws 11. These are provided to enable a safe latching engagement with the locking ring 3, as illustrated in FIGS. 5a, 5b, 5c. Resilient joints 13 on the claw ring 1 allow the claws 11 to spread when they snappingly engage with the locking ring 3.

Figure 3:
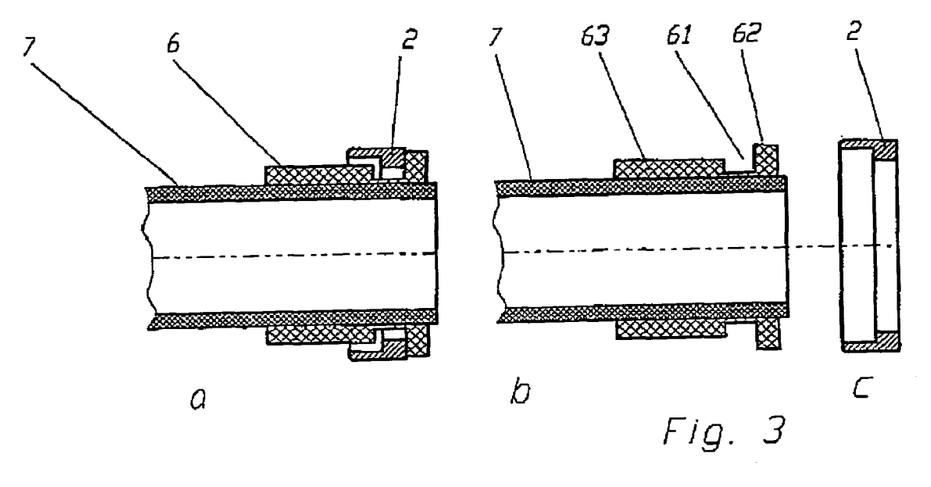

FIGS. 3a, 3b, 3c depict the cannula end 71 of the cannula 7. In FIG. 3a, the reinforcement element 6 is applied to the cannula end 71, with the spacer ring 2 being located in the groove 61 of the reinforcement element 6. FIG. 3b shows the cannula end 71 without a spacer ring 2, but with a reinforcement element 6 with a formed tension ring 63, collar 62 and groove 61. FIG. 3c shows the spacer ring 2 which can be formfittingly inserted into the groove 61 of the reinforcement element 6.

Figure 4:
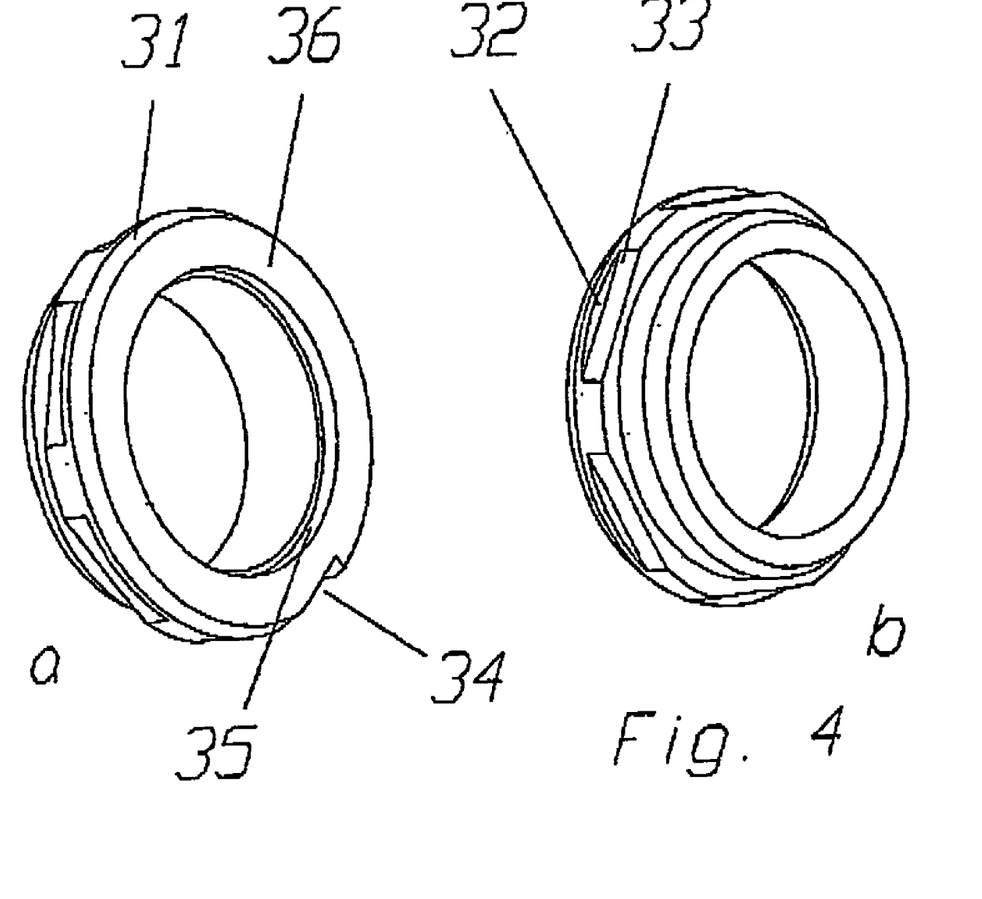

FIGS. 4a and 4b show an individual locking ring 3. Also shown are a sloped locking ring face 31, a locking ring holding face 32, a sloped unlatching faces 33, a rotation limit stop 34, a clearance 35 and an end face 36 which can function as an axial sealing surface. FIG. 4a shows a view in the direction of the tube 5, whereas FIG. 4b shows a view in the direction of the cannula 7.

FIGS. 5a, 5b, 5c depict a claw ring 1 and a locking ring 3 in an unlatched (or not-snapped-in) state (FIGS. 5a and 5b) and in a latched (or snapped-in) state (FIG. 5c). Clearly seen is the cooperation between the resilient joints 13 of the claw support faces 12 and the sloped claw surface 14 of the claw ring 1 with the sloped face 31, the holding surface 32, the sloped face for unlatching 33, as well as the clearance 35.

FIG. 6a shows the latched state after the claw ring 1 is pushed onto the locking ring 3. The unlatching position is reached by rotating the claw ring 1 to a rotation limit stop 34, wherein the claws 11 are spread apart when sliding on the sloped unlatching faces 33 of the locking ring 3 (FIG. 6b). The claw ring 1 can now be pulled off the locking ring 3 in the axial direction and the cannula 7 can be pulled from the hose coupling, thereby releasing the connection.

FIGS. 7a and 7b illustrate the arrangement of several reinforcement elements 6 onto cannula 7 for advantageously matching the length during implantation. Depending on the anatomy, the length of the cannula 7 is shortened by cutting of a certain number of the structure reinforcement elements 6 during surgery. The so formed cannula shoulder 72 extends into the clearance 35 of the locking ring 3 when the cannula 7 and the tube 5 are joined. FIG. 7b shows a cannula with reinforcement elements 6 that form an integral part of the cannula (produced by injection molding).

Possible boundaries for matching to the size requirements during implantation are indicated by A-B and C-D.

Figure 8:
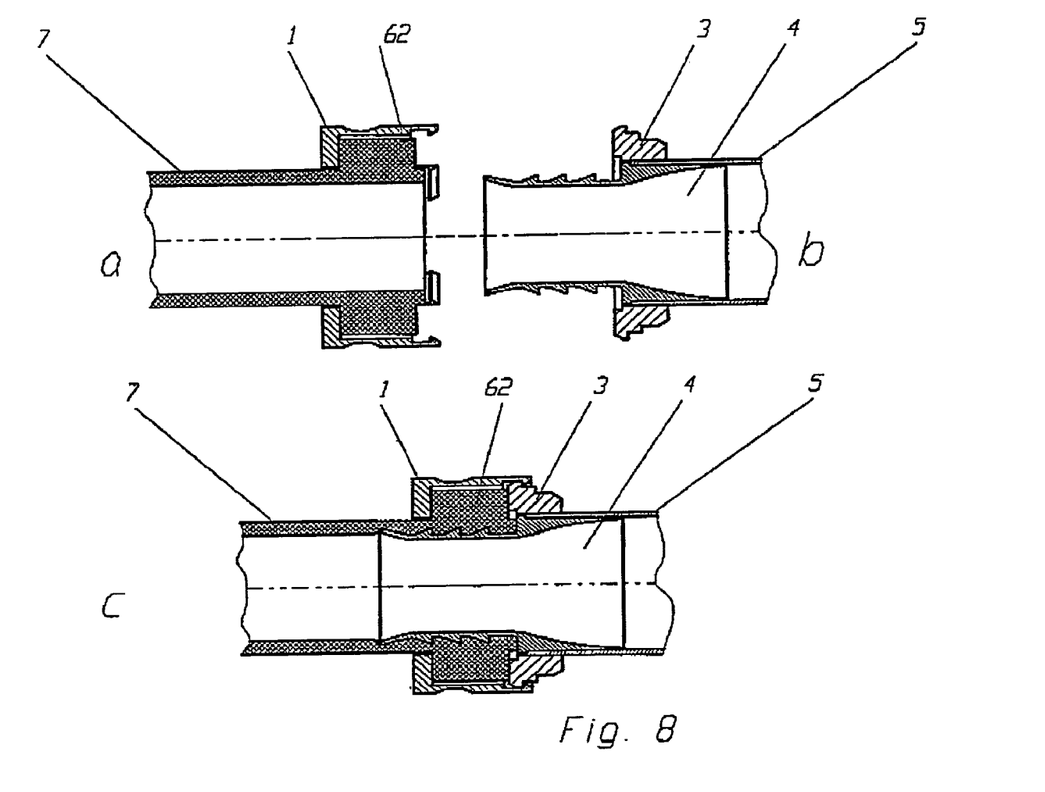

FIGS. 8a, 8b and 8c show another embodiment of the device according to the invention. FIG. 8a depicts the cannula end 71 of the cannula 7 with locking ring 1 and collar 62 which is herein formed directly on the cannula end 71. This embodiment does not include a reinforcement element 6.

FIG. 8b illustrates the tube end 51 of the tube 5 which includes the locking ring 3 and the hose coupling 4. By inserting the hose coupling 4 into the cannula end 71, a tight connection is produced between the two members as a result of the latching engagement between the claw ring 1 and the locking ring 3. The collar 62 is relatively wide so that the radial sealing forces are enhanced together with the axial seal at the contact surfaces of the ends.

Figure 9:
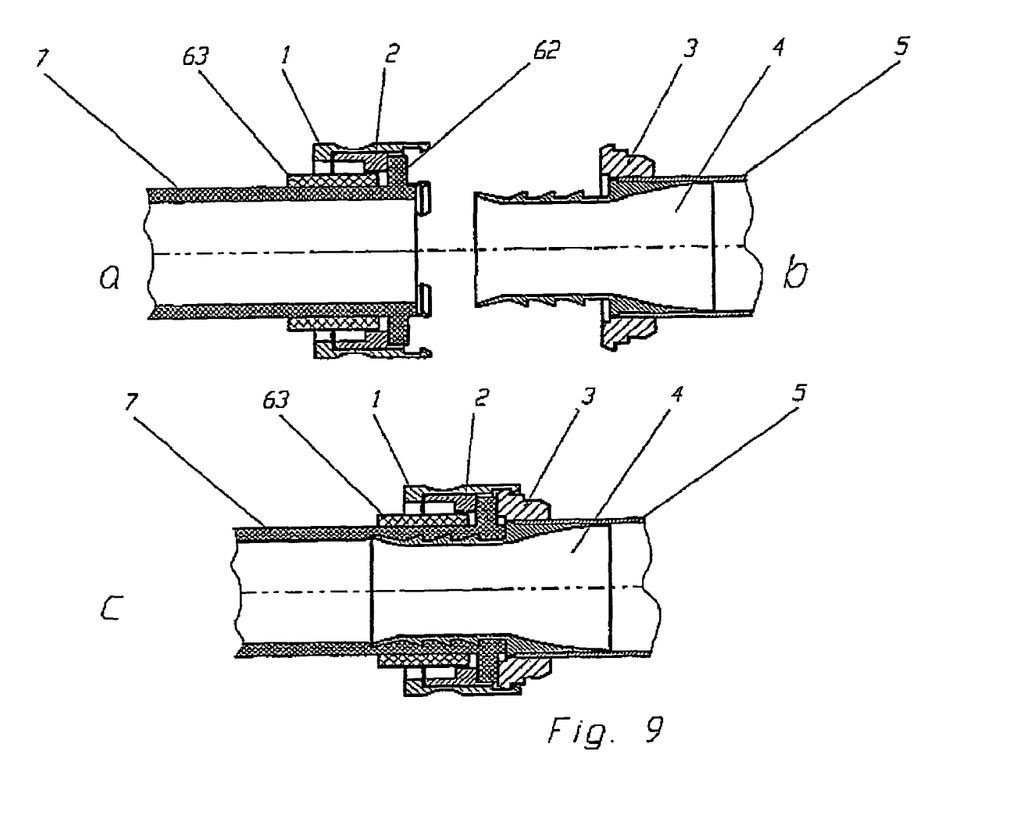

FIGS. 9a, 9b and 9c show another embodiment of the device according to the invention. Instead of a closed reinforcement element 6, an arrangement with a separate collar 62, tension ring 63 and spacer ring 2 is used. This embodiment also achieves a secure connection and tight seal.

Figure 10:
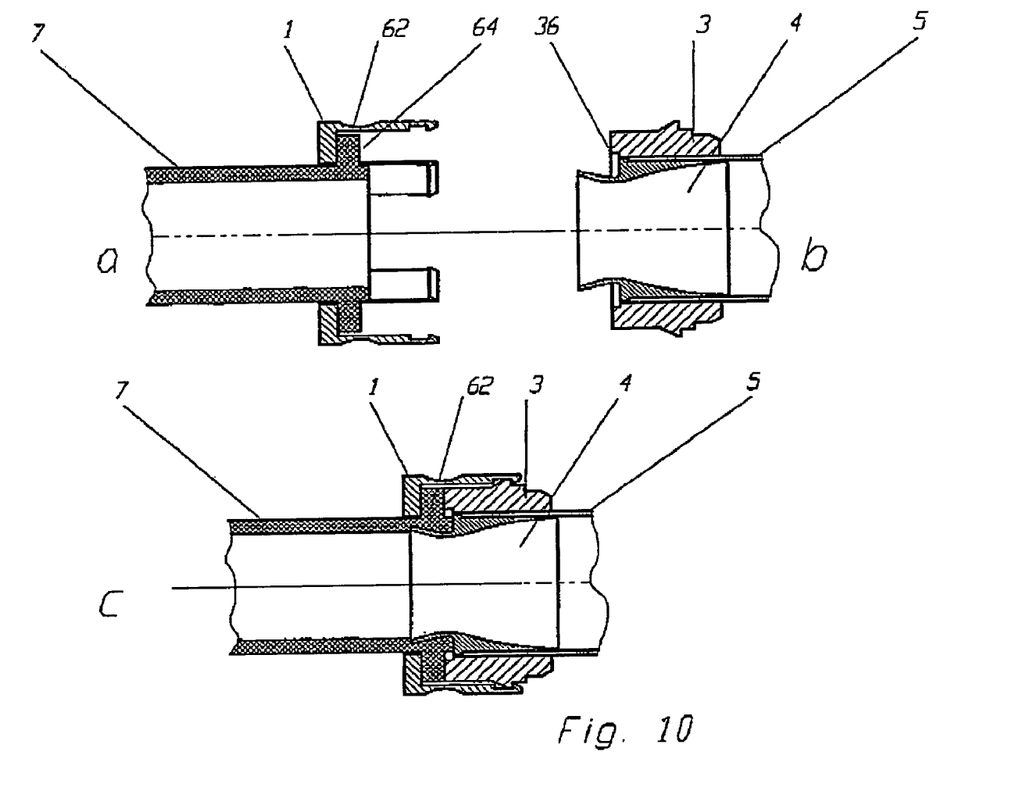

FIGS. 10a, 10b and 10c show yet another embodiment of the device according to the invention. The hose coupling 4 is herein noticeably shorter, whereas the locking ring 3 is wider.

Figure 11:
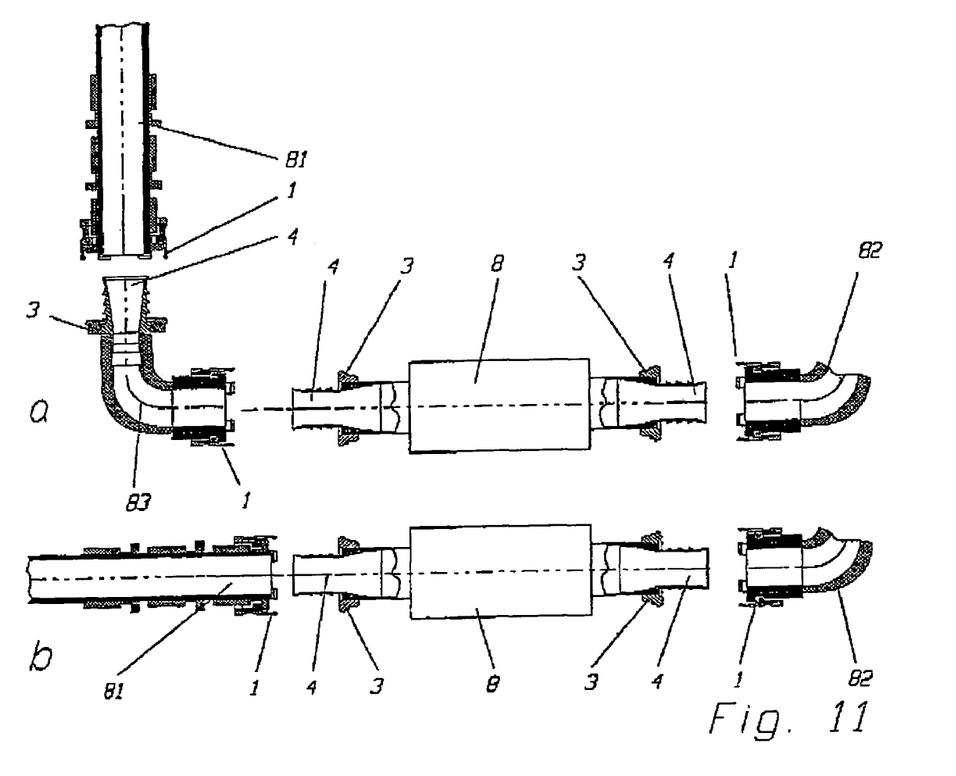

FIGS. 11a and 11b show schematically an application of the device of the invention with an implantable blood pump. A secure connection can be established to the outlet elbow 83 with the device according to the invention by latching the claw ring 1 on the locking ring 3. On the other side of the pump 8, an inlet cannula can be connected to the pump by likewise latching the claw ring 1 on the locking ring 3. In addition, the outlet elbow can be connected at the other end with a so-called outlet cannula 81. The significant advantage of this arrangement is easily seen from the diagram of FIG.

11a. An optimal position can be achieved by rotating the elbow, without impeding the connectivity with the pump 8 in any way.

FIG. 11b shows the connection of the pump 8 having the hose coupling 4 to the outlet cannula 81 and the inlet cannula 82 without using an outlet elbow 83. The outlet cannula 82 has several reinforcement elements 6 successively arranged on the cannula end 71 (FIGS. 7a and 7b).

Advantageously, the device can be utilized in particular with a blood pump 8 which is implanted in the body and has to be connected with inlet and outlet cannulae 82 and 81. Both the inlet and the outlet cannula 82 and 81 are connected to the pump system with the snap connector according to the invention. Blood coming from the heart is supplied to the blood pump 8 via the inlet cannula 82 and then flows from the blood pump 8 via the outlet cannula 82 to the aorta (not shown). Inlet and outlet cannulae 82 and 83 are connected to the blood pump 8 by the device according to the invention. The outlet elbow 83 can optionally be inserted between the blood pump 8 and the outlet cannula 81. The inlet of the outlet elbow 83 is configured like a cannula end 71 and can hence also be secured to the pump outlet by a snap connector. The outlet of the outlet elbow 83 includes the hose coupling 4 and can therefore be connected to the outlet cannula 81 by using an additional snap connector (FIG. 11a).

When the heart assist system is implanted, the system can be adapted to the corresponding physical body size by cutting off at least one reinforcement element 6, as shown in FIG. 7a. The claw ring 1 and the spacer ring 2 (FIG. 1) can be easily pushed on the following reinforcement element 6 by suitably deforming the elastic material.

The invention claimed is:

1. A connection system for use in medical applications comprising:
   a cannula made of a flexible material, a claw ring disposed on the cannula and having at least two claws (11), wherein the claw ring encompasses an outer surface of the cannula and is arranged on a cannula end (71) of the cannula for rotation and axial displacement on the cannula to a stop, the stop comprising a collar (62) on the cannula end (71) on the outer surface of the cannula, and
   a tube (5) comprising a locking ring (3) attached to a tube end (51) and a nipple attached to the tube, wherein the claw ring (1) is capable to be joined with the locking ring (3) by an axial movement of the claw ring (1) with respect to the cannula (7) towards the locking ring (3) and by latching of the at least two claws (11) on the locking ring (3) in a position in which this axial movement is limited by the stop.

2. The system according to claim 1, wherein the system further comprises a tension ring (63) disposed on the cannula end (71), with the claw ring (1) being arranged for displacement and rotation on the tension ring (63).

3. The system according to claim 2, wherein the tension ring (63) is made of an elastic material.

4. The system according to claim 3, wherein the elastic material is silicone.

5. The system according to claim 2, wherein the tension ring (63) is made of an inflexible material.

6. The system according to claim 5, wherein the inflexible material is metal.

7. The system according to claim 2, wherein the tension ring (63) comprises a slotted sleeve.

8. The system according to claim 1, wherein the stop comprises a spacer ring (2), capable of rotation and displacement, which is arranged before the collar (62).

9. The system according to claim 8, wherein a reinforcement element (6) is firmly connected with the cannula end (71) and adapted for displacement and rotation of the claw ring (1) on the reinforcement element (6).

10. The system according to claim 9, wherein the reinforcement element (6) comprises a tension ring (63) and the collar (62).

11. The system according to claim 10, wherein the reinforcement element (6) includes a groove (61) disposed between the tension ring (63) and the collar (62).

12. The system according to claim 11, wherein the spacer ring (2) is arranged in the groove (61) of the reinforcement element (6).

13. The system according to claim 8, wherein the claw ring (1) includes a base ring (15), and the at least two claws comprise claw holding surfaces (12) extending from the base ring (15) and connected to the base ring (15) via resilient joints (13).

14. The system according to claim 13, wherein the spacer ring (2) is firmly connected with the base ring (15).

15. The system according to claim 9, wherein the reinforcement element (6) is made of a flexible material.

16. The system according to claim 9, wherein the reinforcement element (6) and the cannula (7) are made of the same flexible material.

17. The system according to claim 10, wherein the claw ring (1) is arranged on the tension ring (63) of the reinforcement element (6) so as to be rotatable and displaceable in an axial direction to the stop.

18. The system according to claim 1, wherein the locking ring (3) secured on the tube end (51) comprises a sloped locking ring face (31) and locking ring holding faces (32).

19. The system according to claim 1, wherein the locking ring (3) includes sloped unlatching faces (33).

20. The system according to claim 1, wherein the locking ring (3) includes at least one rotation limit stop (34).

21. The system according to claim 1, wherein the locking ring (3) includes a clearance (35).

* * * * *